US012038383B2

(12) United States Patent
Pandey et al.

(10) Patent No.: US 12,038,383 B2
(45) Date of Patent: Jul. 16, 2024

(54) METHOD AND SYSTEM FOR IDENTIFYING TISSUE TYPE BASED ON PEAK-FITTED PARAMETERS IN HIGH-WAVENUMBER RAMAN SPECTRUM

(71) Applicant: CytoVeris Inc., Farmington, CT (US)

(72) Inventors: Rishikesh Pandey, Unionville, CT (US); Alan Kersey, South Glastonbury, CT (US)

(73) Assignee: CytoVeris Inc., Farmington, CT (US)

( * ) Notice: Subject to any disclaimer, the term of this patent is extended or adjusted under 35 U.S.C. 154(b) by 0 days.

(21) Appl. No.: 17/688,776

(22) Filed: Mar. 7, 2022

(65) Prior Publication Data

US 2022/0283092 A1 Sep. 8, 2022

Related U.S. Application Data

(60) Provisional application No. 63/157,357, filed on Mar. 5, 2021.

(51) Int. Cl.
*G01N 21/65* (2006.01)
*A61B 5/00* (2006.01)
(Continued)

(52) U.S. Cl.
CPC ........... *G01N 21/65* (2013.01); *A61B 5/0071* (2013.01); *A61B 5/0075* (2013.01);
(Continued)

(58) Field of Classification Search
CPC .. G01N 21/65; G01N 21/6486; A61B 5/0071; A61B 5/0075; A61B 5/0086; G01J 3/44; G16H 50/20
See application file for complete search history.

(56) References Cited

U.S. PATENT DOCUMENTS

| 7,499,153 | B2 | 3/2009 | Puppels |
| 8,326,404 | B2 | 12/2012 | Zeng |
| 2022/0187209 | A1* | 6/2022 | Oh .......................... G01N 21/65 |

OTHER PUBLICATIONS

Aubertin, Kelly, et al. "Combining high wavenumber and fingerprint Raman spectroscopy for the detection of prostate cancer during radical prostatectomy." Biomedical Optics Express 9.9 (2018): 4294-4305. Note: for reference with pages numbers (Year: 2018).*
(Continued)

*Primary Examiner* — Tarifur R Chowdhury
*Assistant Examiner* — Carlos Perez-Guzman
(74) *Attorney, Agent, or Firm* — Getz Balich LLC (57) ABSTRACT

A method and system for identifying tissue types is provided that utilizes Raman scattered light in the high wavenumber region (HWN) of Raman spectrum. The method includes: a) interrogating a tissue specimen with at least one wavelength of light, the wavelength of light operable to produce Raman scattered light in a HWN region of Raman spectrum from the tissue specimen; b) producing signal data representative of the Raman scattering, the signal data relating signal intensity as a function of wavenumber within the HWN region; c) fitting a curve to a portion of the signal data attributable to a HWN peak within the signal data, for a plurality of different HWN peaks; d) determining a plurality of characteristics of each fitted curve; and e) determining a tissue type using the determined characteristics and stored collective data representative of fitted peaks in the HWN region of a plurality of different tissue types.

22 Claims, 8 Drawing Sheets

(51) Int. Cl.
G01J 3/44 (2006.01)
G01N 21/64 (2006.01)
G16H 50/20 (2018.01)

(52) U.S. Cl.
CPC .............. *A61B 5/0086* (2013.01); *G01J 3/44* (2013.01); *G01N 21/6486* (2013.01); *G16H 50/20* (2018.01)

(56) References Cited

OTHER PUBLICATIONS

A. S. Haka, et al., "In vivo margin assessment during partial mastectomy breast surgery using Raman spectroscopy," Cancer Res. 66(6), 3317-3322 (2006).

Aubertin et al., "Combining high wavenumber and fingerprint Raman spectroscopy for the detection of prostate cancer during radical prostatectomy", 9, (9), Biomedical Optics Express, p. 4294, (2018).

J. Mo, et al., "High wavenumber Raman spectroscopy for in vivo detection of cervical dysplasia," Anal. Chem. 81(21), 8908-8915 (2009).

K. Lin, et al., "Optical diagnosis of laryngeal cancer using high wavenumber Raman spectroscopy," Biosens. Bioelectron. 35(1), 213-217 (2012).

Pandey et al. "Raman spectroscopy based molecular bar coding: realizing the value of high wavenumber region in breast cancer detection", Proc. SPIE 11631, Advanced Biomedical and Clinical Diagnostic and Surgical Guidance Systems XIX, 1163105 (Mar. 5, 2021); https://doi.org/10.1117/12.2578933.

Wang et al., "Simultaneous fingerprint and high-wavenumber fiber-optic Raman spectroscopy improves in vivo diagnosis of esophageal squamous cell carcinoma at endoscopy", Scientific Reports, 5, Article No. 12957 (2015).

* cited by examiner

METHOD AND SYSTEM FOR IDENTIFYING TISSUE TYPE BASED ON PEAK-FITTED PARAMETERS IN HIGH-WAVENUMBER RAMAN SPECTRUM

This application claims priority to U.S. Patent Application No. 63/157,357 filed Mar. 5, 2021, which is hereby incorporated by reference in its entirety.

BACKGROUND OF THE INVENTION

1. Technical Area

The present disclosure relates to systems and methods for examining a biological sample using Raman spectroscopy in general, and more specifically to such systems and methods operating in the high wavenumber region in particular.

2. Background Information

Raman spectrum of interest in biological sample analysis includes two primary regions of interest: the "Fingerprint" or "FP" region and the "High Wavenumber" or "HWN" region. The FP region typically includes a wavenumber range of about 400 $cm^{-1}$ to about 1800 $cm^{-1}$ and the HWN region typically includes a wavenumber range of about 2800 $cm^{-1}$ to about 3800 $cm^{-1}$. The FP region typically comprises a series of multiple peaks and is rich in Raman spectral information. In the case of biological samples, the FP region contains information on the relative content of biomolecular components, such as DNA, proteins, phospholipids, lipids, and the like. Research based on the FP region alone has demonstrated the detection of cancerous tissue [1]. The HWN region typically includes a composite broad spectral shape that includes several underlying peaks associated with different biomolecules. Recent work in the HWN range has demonstrated successful classification of cancerous tissue versus normal tissue with high sensitivity and specificity [2, 3, 4, 5, 6]. The Raman spectral features from tissue in HWN are typically unaffected by Raman signals from the glass as well as from tissue marking dye. It has been shown that combining information from the FP and HWN regions can lead to enhanced performance for some applications [7]. A molecular barcoding approach discerning tissue types in the HWN region has also been reported [8].

SUMMARY OF THE INVENTION

According to an aspect of the present disclosure, a method of identifying tissue types that utilizes Raman scattered light in the high wavenumber region of Raman spectrum is provided. The method includes: a) interrogating a tissue specimen with at least one wavelength of light, the at least one wavelength of light operable to produce Raman scattered light in a high wavenumber (HWN) region of Raman spectrum from the tissue specimen upon the at least one wavelength of light being incident to the tissue; b) producing signal data representative of the Raman scattering, the signal data relating signal intensity as a function of wavenumber within the HWN region; c) fitting a curve to a portion of the signal data attributable to a HWN peak within the signal data, for a plurality of different HWN peaks; d) determining a plurality of characteristics of each fitted curve; and e) determining a tissue type using the determined characteristics of the fitted curves and stored collective data representative of fitted peaks in the HWN region of a plurality of different tissue types.

According to another aspect of the present disclosure, a system for identifying tissue types is provided that includes at least one light source, a spectrometer or a monochromator, at least one light detector, and a system controller. The system controller is in communication with the light source, the light detector, and a non-transitory memory storing instructions. The instructions when executed cause the system controller to: a) control the light source to interrogate a tissue specimen at one or more predetermined wavelengths; b) control the light detector to sense scattered light emanating from the tissue specimen after the scattered light has been processed by the spectrometer or the monochromator, the scattered light resulting from the light interrogation of the subject tissue, and to produce signal data representative of a Raman spectrum in the high wavenumber (HWN) region based on the sensed light; c) process the signal data into processed signal data, the processed signal data relating scattered light signal intensity as a function of wavenumber within the HWN region; d) fit a curve to a portion of the processed signal data attributable to a HWN peak within the processed signal data, for a plurality of different HWN peaks; e) determine a plurality of characteristics of each fitted curve; and f) determine a tissue type using the determined characteristics of the fitted curves and stored collective data representative of fitted peaks in the HWN region of a plurality of different tissue types.

In any of the aspects of embodiments described above and herein, at least one of the fitted HWN peaks may be representative of Raman scattered light produced by a biomolecule or a set of biomolecules present in the tissue specimen.

In any of the aspects of embodiments described above and herein, the biomolecule present in the tissue specimen may be a lipid, a protein, DNA, a phospholipid, or a fatty acid, or any combination thereof.

In any of the aspects of embodiments described above and herein, the signal data relating signal intensity as a function of wavenumber may be produced within a portion of the HWN region between about 2800 $cm^{-1}$ to about 3050 $cm^{-1}$.

In any of the aspects of embodiments described above and herein, the plurality of characteristics of each fitted curve may include an area under the respective fitted curve.

In any of the aspects of embodiments described above and herein, the step of determining a plurality of characteristics of each fitted curve may include determining an area plot for each of a plurality of different tissue types at one or more respective wavenumbers within the HWN region, wherein each area plot is based on the signal data relating signal intensity as a function of the respective wavenumber within the HWN region.

In any of the aspects of embodiments described above and herein, the plurality of different tissue types may include adipose tissue, benign tissue, and cancer tissue.

In any of the aspects of embodiments described above and herein, the plurality of different characteristics of each fitted curve as represented by an area plot may include at least one of an area, width, or height of the fitted curve.

In any of the aspects of embodiments described above and herein, the stored collective data representative of fitted peaks in the HWN region of a plurality of different tissue types may be based on data collected from a statistically significant number of tissue specimens.

In any of the aspects of embodiments described above and herein, the instructions when executed may cause the system controller to determine an area plot for each of a plurality of different tissue types at one or more respective wavenumbers within the HWN region, wherein each area plot may be based on the processed signal data relating signal intensity as a function of the respective wavenumber within the HWN region.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DETAILED DISCLOSURE

Figure 1:
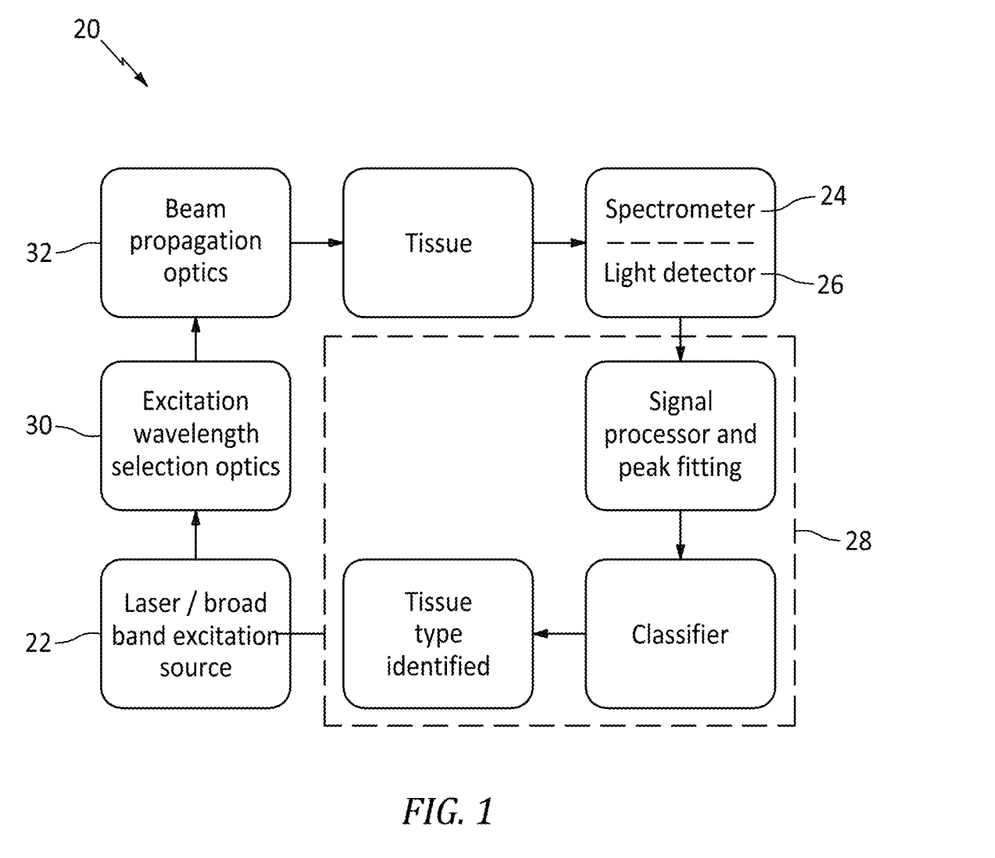
FIG. 1 is a diagrammatic representation of a present disclosure system embodiment.

Referring to FIG. 1, the present disclosure includes a method and system for automated identification/classification of tissue based on Raman spectra in the high wavenumber region (HWN) of the Raman spectrum. Embodiments of the present disclosure system 20 may include a light source 22, a spectrometer or monochromator 24, a light detector 26, and a system controller 28.

The light source 22 is configured to emit light at a plurality of wavelengths that will produce Raman spectra in the HWN region when interrogating a tissue specimen. The present disclosure may use a variety of different light source types and is not limited to any particular type of light source 22. Non-limiting examples of light source 22 types include lasers, tunable lasers, and broad band light sources. The example system 20 diagrammatically shown in FIG. 1 indicates that the light source 22 may include a laser or a broad band light source. Non-limiting examples of an acceptable laser that may be used, for example, include solid state, gas, diode laser or vertical-cavity surface-emitting lasers (VCSELs). The present disclosure may utilize light for interrogation purposes at a variety of different wavelengths, and the light source 22 is therefore not limited to producing light at any particular wavelength or wavelength band.

In some embodiments, a present disclosure system 20 may include optical elements operable to form or otherwise manage the light produced by the light source 22. For example, the present disclosure system 20 shown in FIG. 1 includes excitation wavelength selection optics 30 and beam propagation optics 32. These are non-limited examples of optical elements operable to form and/or manage the light that is used to interrogate the tissue sample and the present disclosure is not limited thereto.

Embodiments of the present disclosure may include a spectrometer or a monochromator (referred to hereinafter as a "spectrometer 24" to facilitate the description) coupled with a light detector 26. The spectrometer 24 may be configured to receive and process light emanating from the tissue (e.g., Raman scattered light and fluorescent emissions) as a result of the tissue being interrogated with light from the light source 22. The light detector 26 receives the processed light spectrum from the spectrometer 24, produces signals representative thereof, and communicates those signals to the system controller 28. Non-limiting examples of a light detector type that may be used include a light sensor that converts light energy into an electrical signal such as a camera, a simple photodiode, a CCD array, or the like.

The system controller 28 is in communication with other system 20 components such as the light source 22 and the light detector 26 and may be in communication with other system 20 components. The system controller 28 may be in communication with system 20 components to control the operation of the respective component and/or to receive signals from and/or transmit signals to that component to perform the functions described herein. The system controller 28 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system 20 to accomplish the same algorithmically and/or coordination of system 20 components. The system controller 28 includes or is in communication with one or more memory devices. The present disclosure is not limited to any particular type of memory device, and the memory device may store instructions and/or data in a non-transitory manner. Examples of memory devices that may be used include read-only memory, random access memory, volatile memory, non-volatile memory, static memory, dynamic memory, flash memory, cache memory, and/or any device that stores digital information. The system controller 28 may include, or may be in communication with, an input device that enables a user to enter data and/or instructions, and may include, or be in communication with, an output device configured, for example to display information (e.g., a visual display or a printer), or to transfer data, etc. Communications between the system controller 28 and other system 20 components may be via a hardwire connection or via a wireless connection.

The present disclosure provides a novel and advantageous method and system 20 for identifying and classifying tissue type based on the Raman scattered light in the HWN region. The present disclosure does not identify tissue type directly using intensity/amplitude values of Raman scattered light that are typically inputted to a traditional Raman classifier. In contrast, the present disclosure utilizes collective data parameters based on curves fitted to sensed Raman scattered light intensity values as a function of wavenumber (e.g., Raman shift) in the HWN region, and particularly in the portion of the HWN between about 2800 $cm^{-1}$ to about 3050 $cm^{-1}$.

The present disclosure outlines a new approach of automated identification/classification of tissue type including the disease state in which the classifier is inputted with multiple parameters based on collective data. Non-limiting examples of such parameters include peak area, peak width, peak height, and the like derived from curve fitted peaks in the 2800-3050 $cm^{-1}$ range. The present disclosure is a novel approach that reduces the dimension of the inputted data and thereby simplifies the classification and is less prone to overfitting. There are several advantages to the present disclosure. For example, each respective fitted peak may represent characteristics of a known type/family of biomolecule or a set of similar biomolecules, which in turn makes the classifier interpretable/explainable. As another example, the present disclosure does not require a high-resolution spectrometer 24 making the system 20 cost-effective and/or permits high-throughput; e.g., a spectrometer 24 may be operated under the present disclosure with an increased slit width. Yet another example is that under the present disclosure, classification is less susceptible to spectral artifacts introduced by removing cosmic rays and fluorescence.

Figure 2:
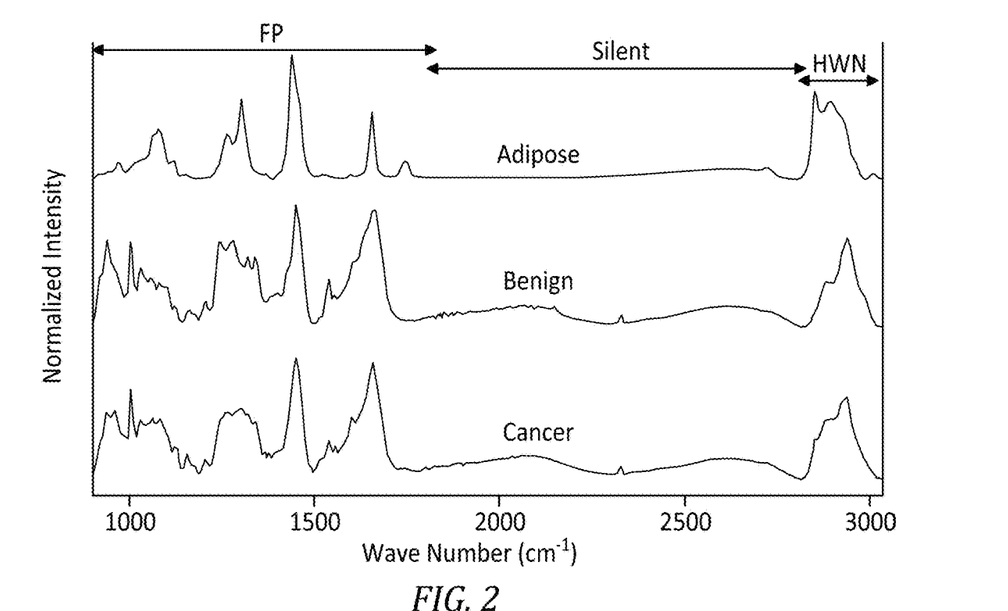
FIG. 2 is a graph of exemplary representative Raman spectra of three major breast tissues showing different regions.
Figure 3:
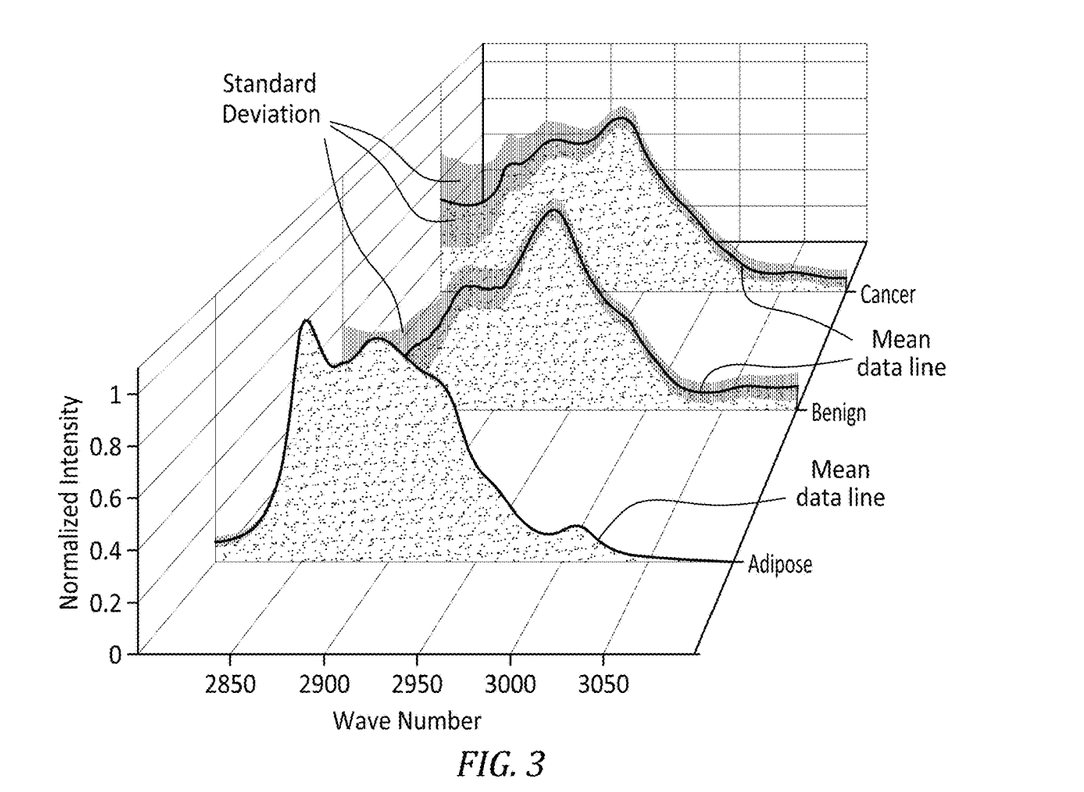
FIG. 3 is a graph of Raman spectra illustrating normalized intensity on the Y-axis and wavenumbers on the X-axis.
Figure 4:
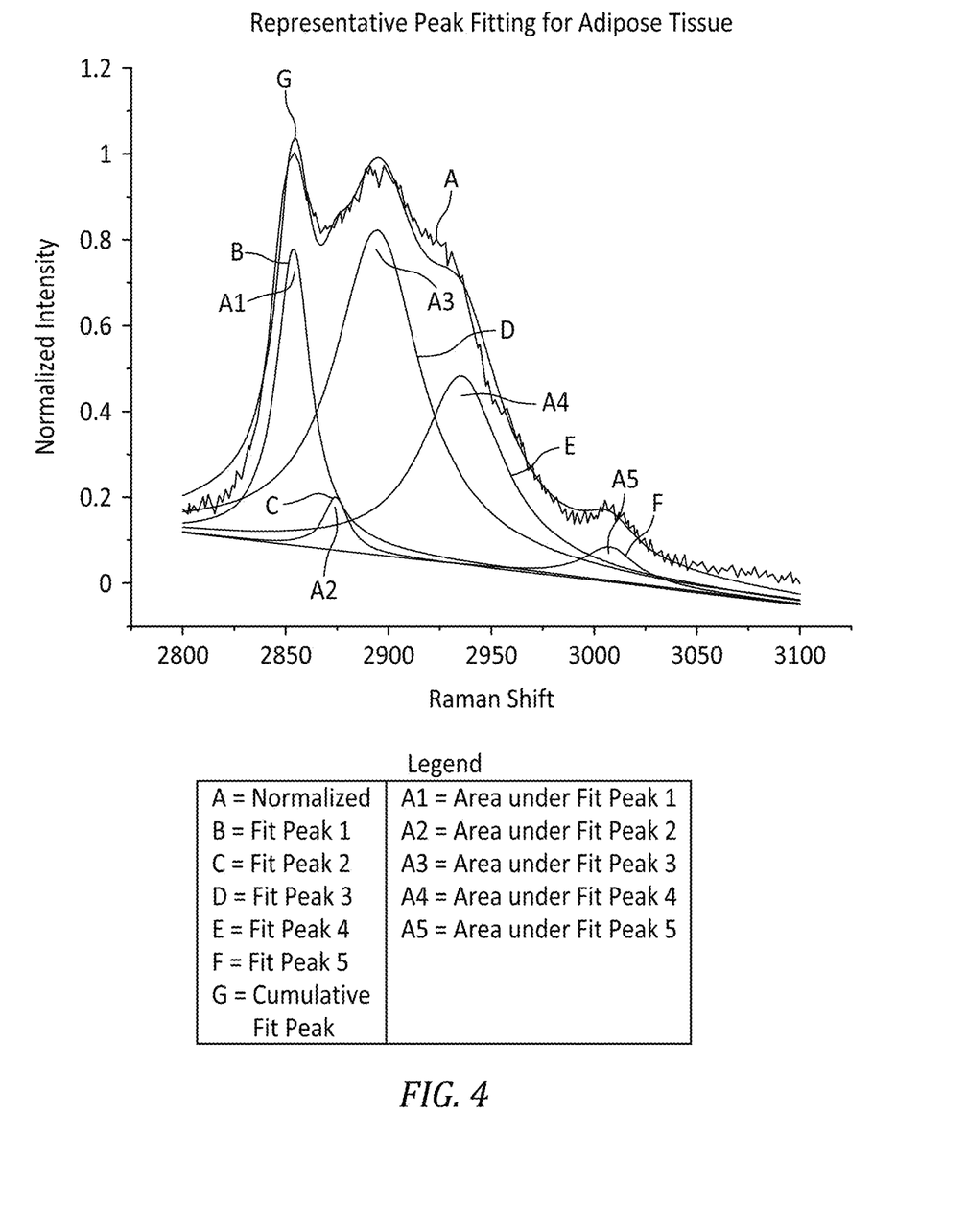
FIG. 4 is a graph of normalized intensity versus wavenumber showing representative peak fitting curves for adipose tissue, showing the broad peak deconvoluted into five peaks.
Figure 5:
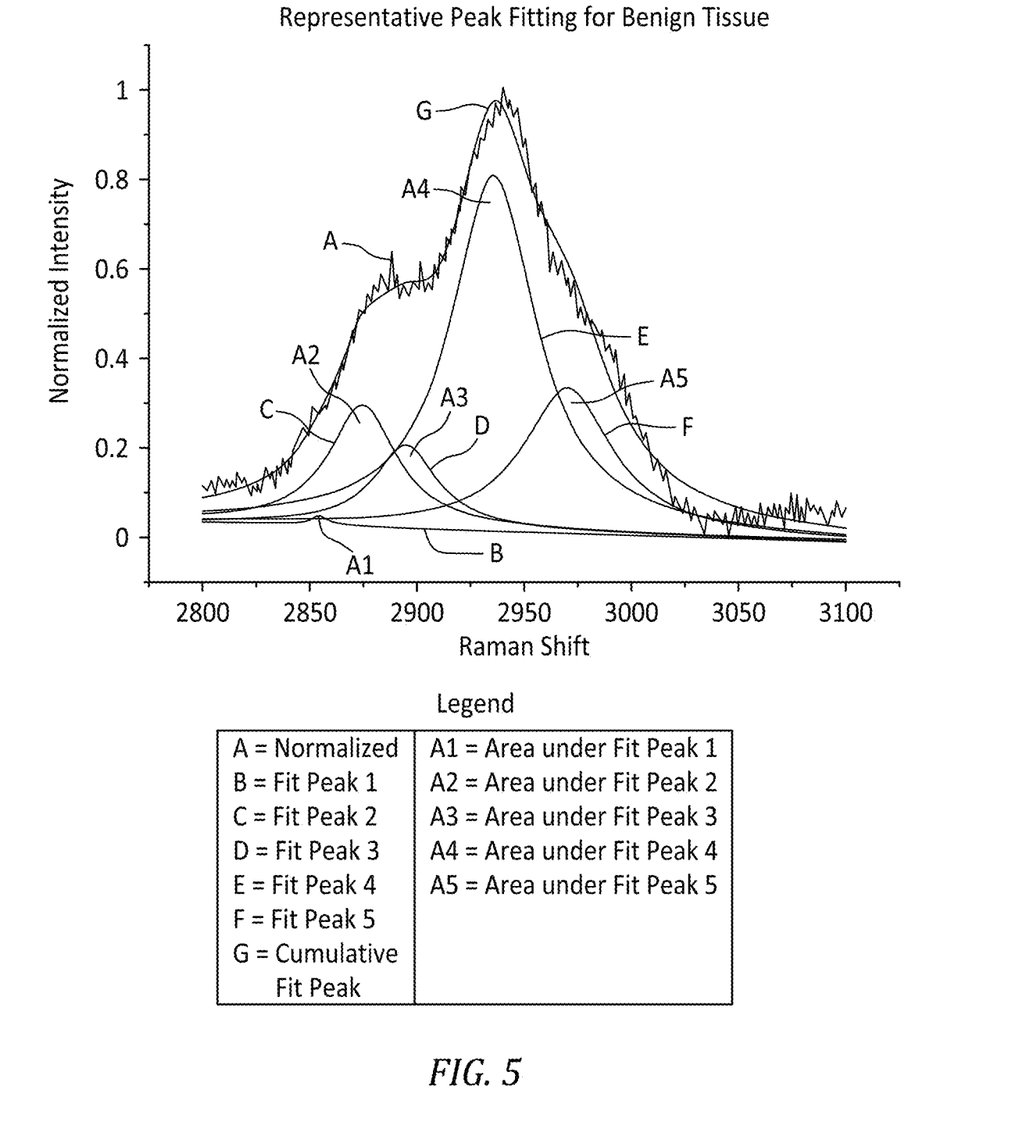
FIG. 5 is a graph of normalized intensity versus wavenumber showing representative peak fitting curves for benign tissue, showing the broad peak deconvoluted into five peaks.
Figure 6:
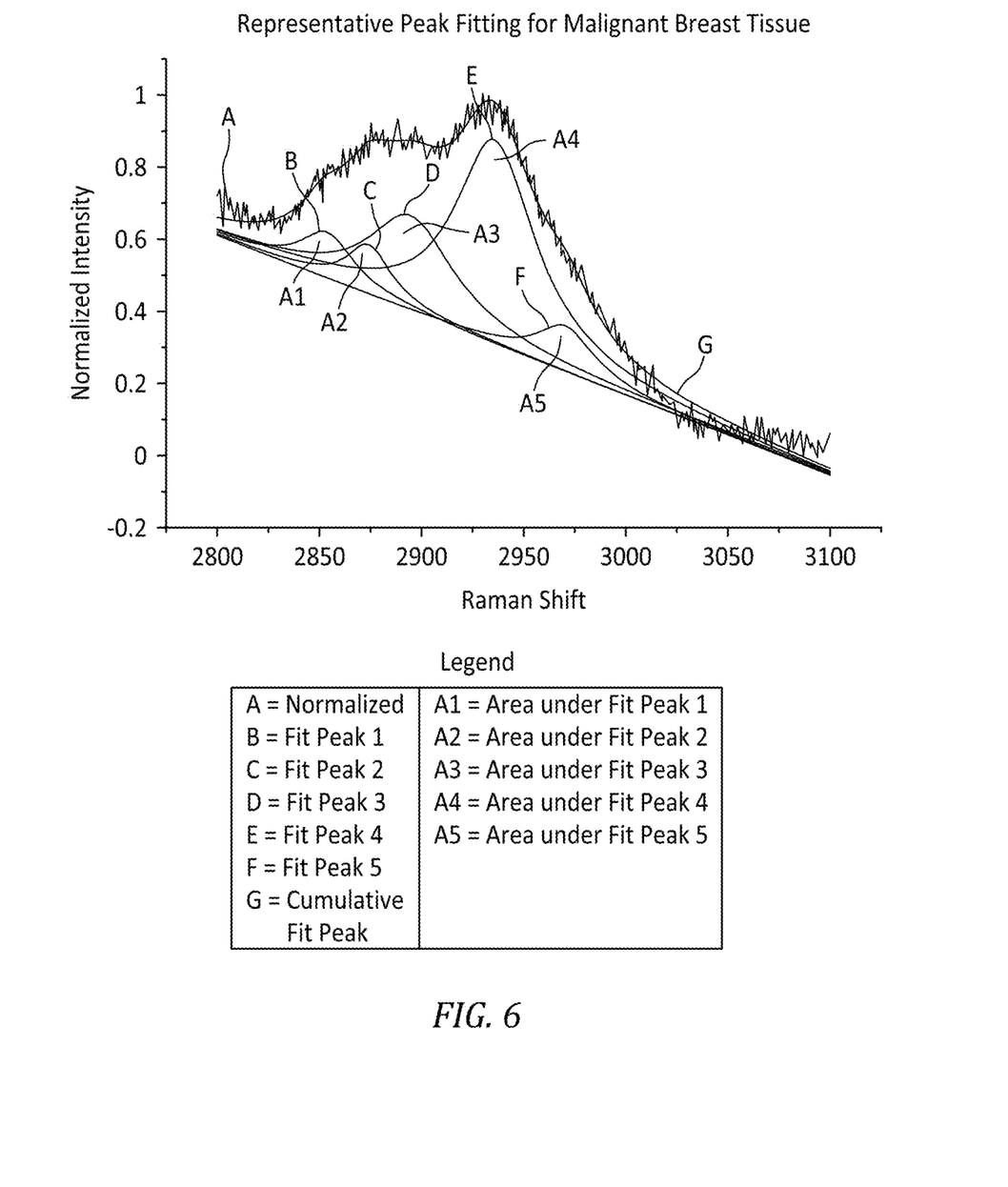
FIG. 6 is a graph of normalized intensity versus wavenumber showing representative peak fitting curves for malignant breast tissue, showing the broad peak deconvoluted into five peaks.

The graph of normalized Raman scattered light intensity versus wavenumber shown in FIG. 2 illustrates the representative Raman spectrum for adipose, benign and cancer human breast tissues within the fingerprint ("FP") region (e.g., about 400 $cm^{-1}$ to about 1800 $cm^{-1}$), the silent region (e.g., about 1800 $cm^{-1}$ to about 2800 $cm^1$), and the high wavenumber ("HWN") region (e.g., about 2800 $cm^{-1}$ to about 3800 $cm^{-1}$). The graph of normalized intensity versus wavenumber in the HWN region shown in FIG. 3 includes a curve representative of data collected from sensing a statistically significant number of tissue specimens. The term "statistically significant" as used herein means that a sufficient amount of data is collected (e.g., from tissue specimens based on intensity versus wavenumber as shown in FIGS. 4-6) to produce a clinically reasonable confidence level that the data is accurate and representative. The dark line in each curve represents the mean normalized intensity value as a function of wavenumber for adipose, benign, and cancer tissue respectively. Each curve also depicts the standard deviation spread in intensity as a function of wavenumber. As can be seen in FIG. 3, the absence of standard deviation in the adipose curve facilitates distinguishing adipose tissue from benign and/or cancer tissue. The standard deviation in the benign and cancer curves in contrast indicates that benign and cancer tissue are less distinguishable from one another.

FIGS. 4-6 illustrate graphs of normalized intensity versus wavenumber for individual specimens of three tissue types (adipose, benign, and malignant human breast tissue). Each graph includes fitted curves for a plurality (5) of different wavenumber peaks within the data represented within each graph. Each respective peak shown within the graphs of FIGS. 4-6 is attributable to a unique/predominant biomolecule. For example, the peak at 2854 $cm^{-1}$ is assigned to C—H vibrations of CH2 and primarily attributed to the lipid content. Similarly, the peak at 2936 $cm^{-1}$ encodes primarily protein content in the tissue. The 3008 $cm^{-1}$ peak is assigned to =C—H vibration and is associated with the lipids and fatty acids. It should be noted that a given peak may not be solely attributable to a particular molecule, but rather may have some amount of contribution from more than one biomolecule. That said, very often a peak will predominated by the contribution of a particular biomolecule.

As is evident from FIGS. 4-6, the fitted peaks (each attributable to a different biomolecule) associated with each tissue type vary based on the presence of the respective biomolecules in the respective tissue types. Hence, the fitted peaks 1-5 in FIG. 4 (adipose tissue) are different from the fitted peaks 1-5 in FIG. 5 (benign tissue) and are different from the fitted peaks 1-5 in FIG. 6 (malignant breast tissue). Importantly, parameters of these fitted peaks 1-5 (e.g., peak area, width, height, etc.) represent data of the type that is used to collectively produce the curves shown in FIG. 3. The parameters of the collective fitted peaks 1-5 in turn may be used in the present disclosure as a means for identifying/classifying the respective tissue types.

FIGS. 4-6 each show a normalized Raman profile ("normalized", referenced as "A") and a curve ("cumulative Fit Peak", referenced as "G") that is fitted to the normalized Raman profile "A". The noisy features indicated in the normalized Raman profiles of the graphs are indicative of the data being from an individual tissue specimens. This is in contrast to the smoother lines representing the mean normalized intensity values shown in FIG. 3. The data shown in FIG. 4 reflects data associated with adipose tissue. The data shown in FIG. 5 reflects data associated with benign tissue. The data shown in FIG. 6 reflects data associated with malignant breast tissue. Each of FIGS. 4-6 show curve fitted peaks "B"-"F" (i.e., "Fit Peaks B-F"). Each of these fitted peaks is representative of a portion of the data reflected in the normalized Raman profile for that tissue specimen; i.e., each fitted peak represents a particular portion of the total sensed intensity indicated by the normalized Raman profile "A", which peak is attributable to a biomolecule present within the tissue specimen sensed. The data used to produce the fitted peaks B-F may be determined using deconvolution techniques or the like. The normalized Raman profile "A" shown in FIGS. 4-6 may either be raw Raman spectrum obtained directly from the spectrometer 24 or it may be preprocessed for baseline correction, cosmic ray removal, smoothing, or the like.

As stated above, parameters of these fitted peaks 1-5 (e.g., peak area, width, height, etc.) from a statistically significant number of tissue specimens may be used in the present disclosure in the identification/classification of the respective tissue types. To facilitate the present description herein, FIGS. 4-6 are also labeled (e.g., A1, A2, A3, A4, A5) to indicate the respective fitted peak areas associated with the respective fitted peaks B-F. As can be seen in FIGS. 4-6 for three different tissue types (adipose, benign, and malignant breast), at different wavenumbers certain of the fitted peaks 1-5 (referenced as B-F) overlap with one another. Hence, at a given wavenumber, the normalized Raman profile "A"/cumulative Fit Peak "G" may include contributions from more than one fitted peak.

Figure 7A:
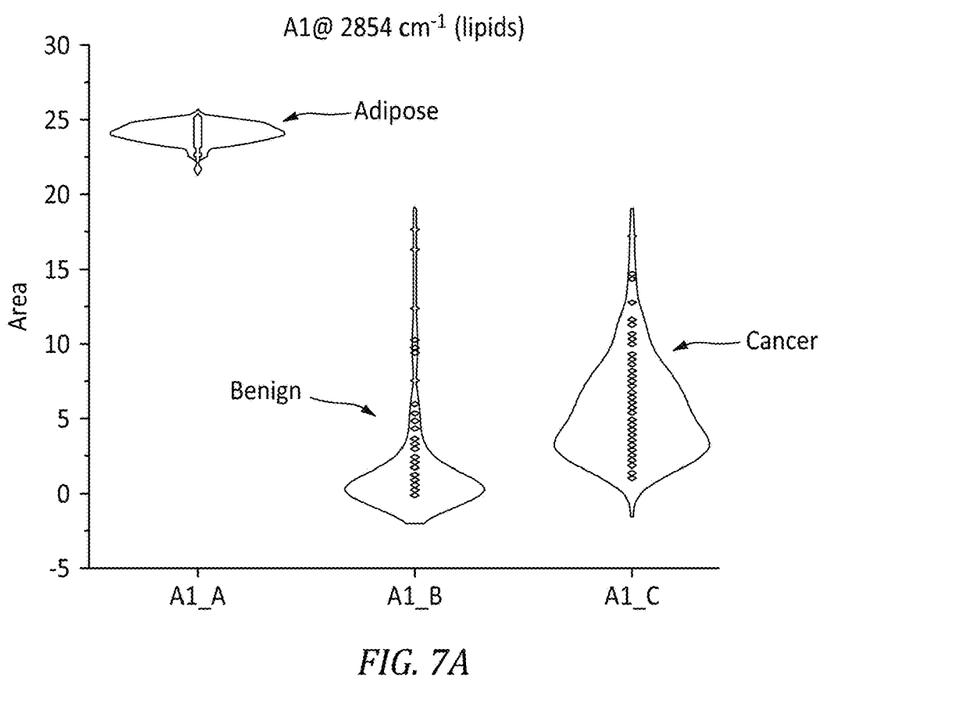
FIG. 7A is graph of area values for adipose, benign and cancer tissue at wavenumber 2854 $cm^{-1}$.
Figure 7B:
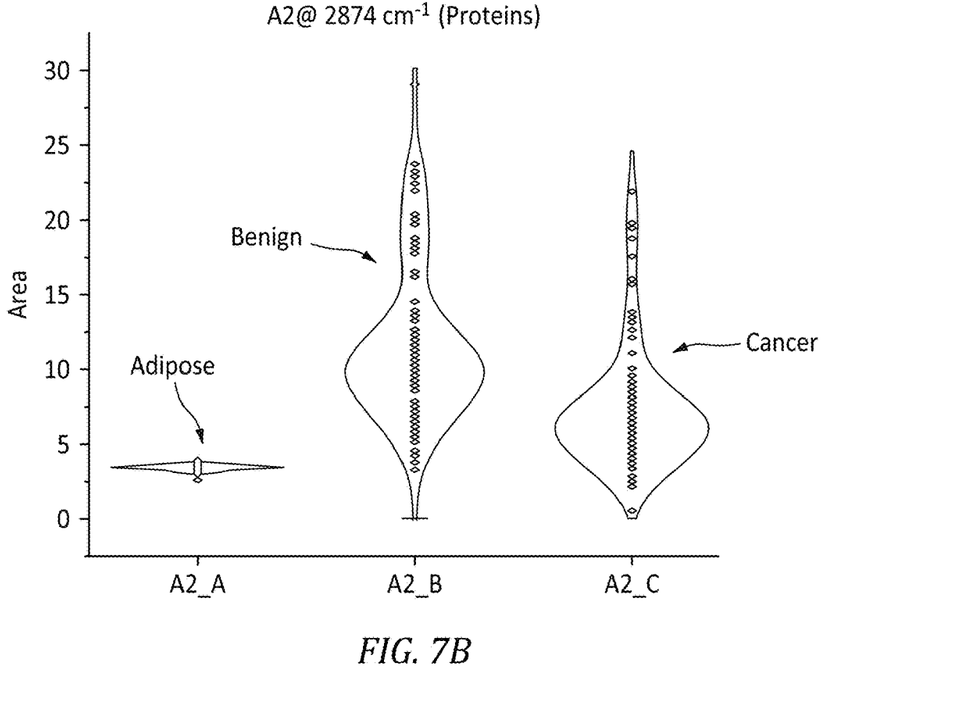
FIG. 7B is graph of area values for adipose, benign and cancer tissue at wavenumber 2874 $cm^{-1}$.
Figure 7C:
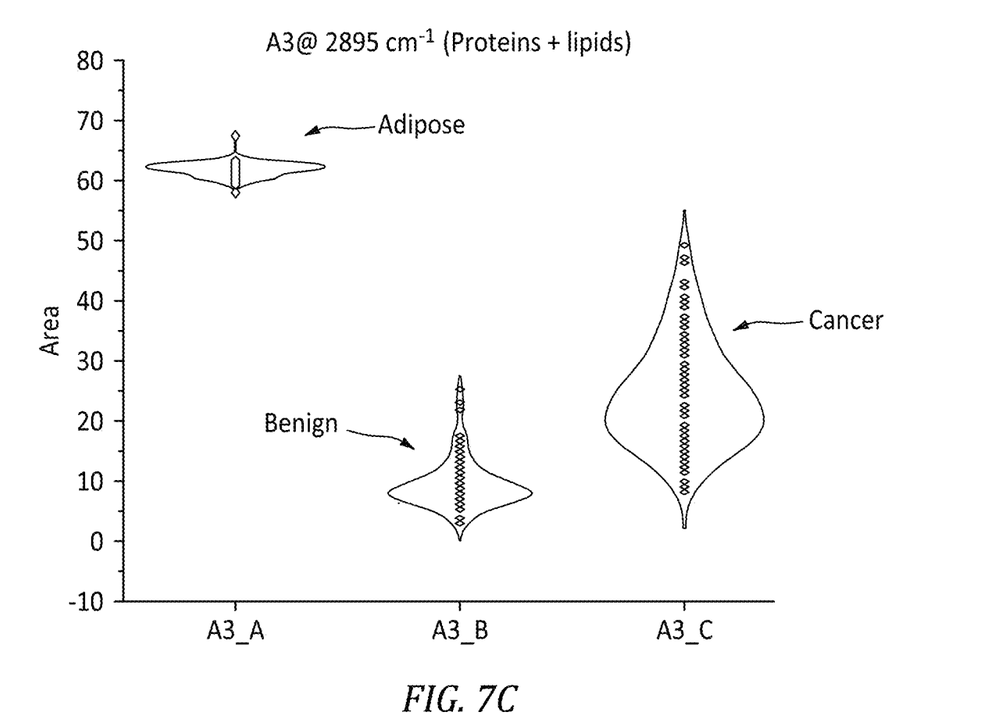
FIG. 7C is graph of area values for adipose, benign and cancer tissue at wavenumber 2895 $cm^{-1}$.

FIGS. 7A-7C graphically illustrate the respective contributions attributable to adipose tissue, benign tissue, and cancer tissue (e.g., malignant breast tissue) at a given wavenumber from a statistically significant number of tissue specimens. In FIGS. 7A-7C, the collective data is shown as area plots. Referring to FIG. 7A, for example, the dots located centrally within each area plot indicate data from individual tissue specimens at about wavenumber 2854 $cm^{-1}$ (which wavenumber is associated with lipids). The height (e.g., Y-axis) of each respective area plot is indicative of the A1 area value spread from normalized intensity value versus wavenumber plots of individual specimens of the respective tissue type (i.e., adipose, benign, cancer) within the collective data. The width (X-axis) of each area plot is indicative of the number of the aforesaid individual specimen plots having that particular area value within the collective data; e.g., wider sections of an area plot are indicative of a larger number of individual specimen plots having that particular area value. The graph of FIG. 7B depicts collective data for each tissue type in the same manner as used in FIG. 7A, except that the collective data is from individual tissue specimens at about wavenumber 2874 $cm^{-1}$ (which wavenumber is associated with lipids and/or proteins). The graph of FIG. 7C depicts collective data for each tissue type in the same manner from individual tissue specimens at about wavenumber 2895 $cm^{-1}$ (which wavenumber is associated with lipids and proteins).

Figure 8:
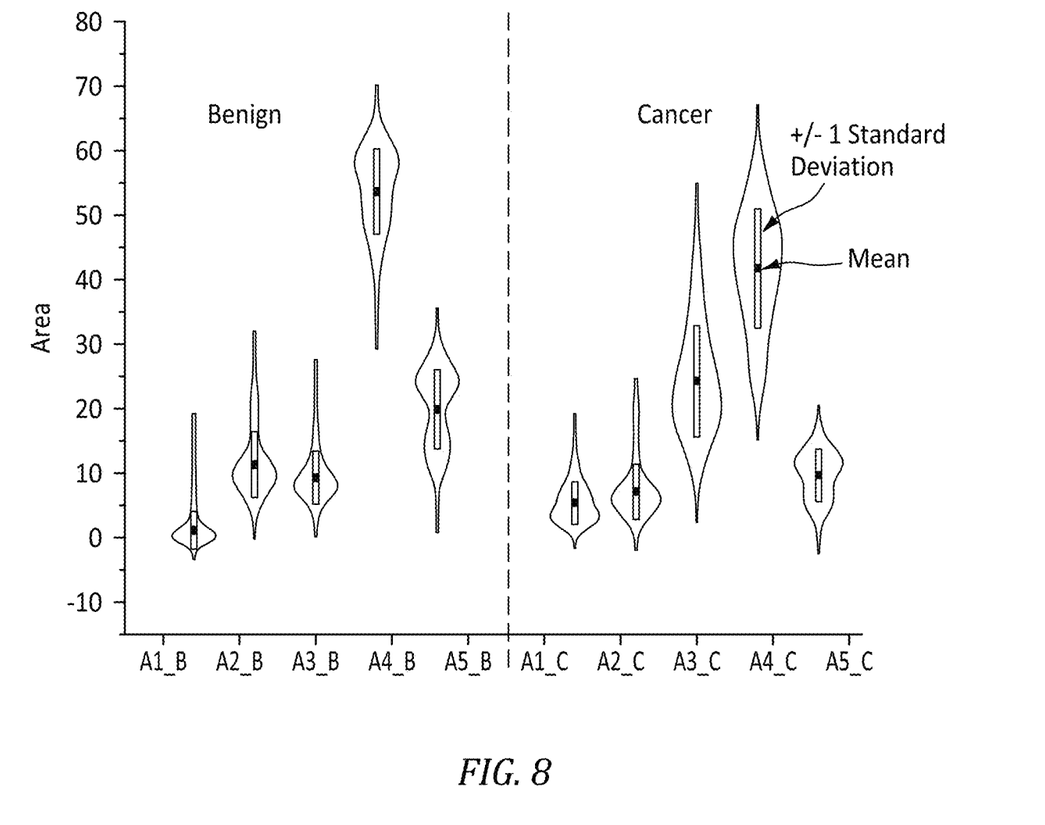
FIG. 8 is a graph of area values of five fitted peaks for benign and cancer tissues.

The area plots shown in FIGS. 7A-7C are a visual representation of the collective data for each tissue type at the respective wavenumbers. FIG. 8 illustrates similar area plots for a plurality of different wavenumber peaks (e.g., A1, A2, A3, etc.) based on collective data for benign tissue and cancer tissue. The area plots shown in FIG. 8 each include a mean peak area value indicator and a standard deviation (+/−one STD) indication. The area plots for each tissue type are distinguishable from other area plots for other tissue types and may be used by the present disclosure as a means to identify/classify tissue types. Each area plot may be characterized as a plurality of determinable data values such as an area value, a peak width value (e.g., FWHM), a height value, mean peak area value indicator, and the like. Hence, the present disclosure is not limited to using a visual representation (e.g., the area plots) of the collective data, but alternatively or in combination may use data values representative of the collective data, and/or algorithmic manipulations of such data values as a means to identify and classify tissue types.

For example, in some embodiments of the present disclosure the aforesaid characterizations of the collective data (e.g., area plots, data values, etc.) may be used by the system controller 28 to identify/classify tissue specimens. The exemplary system 20 shown in FIG. 1, for example, includes a classifier that may be operable (e.g., via stored instructions, including the collective data) to identify/classify tissue specimens using the stored characterizations of the collective data. In some embodiments, the classifier may be based on/utilize machine learning or artificial intelligence; e.g., machine learning or artificial intelligence may be used with characteristic data such area values, a peak width values, height values, and the like. As stated above, in this manner the present disclosure may provide several benefits such as: a) using collective data based on respective fitted peaks representative of biomolecules known to be present within tissue, which in turn makes the classifier interpretable/explainable; b) the present disclosure does not require a high-resolution spectrometer 24 that is typically expensive; c) the present disclosure makes it practical to operate a spectrometer 24 in a high-throughput manner; d) classifications performed by the present disclosure are less susceptible to spectral artifacts, to name a few.

Referring back to FIG. 1, the operation of the exemplary system 20 embodiment shown in FIG. 1 will now be described in greater detail to facilitate understanding of the present disclosure. The system 20 embodiment shown in FIG. 1 includes a light source 22 that may include a plurality of lasers, each configured to produce light centered on a respective wavelength, or a tunable laser, or a broad band excitation source, or the like. Light produced by the light source 22 may be processed by excitation wavelength selection optics and beam propagation optics (collectively referred to hereinafter as the "optics"). For example, for those embodiments that utilize a broad-band light source, the optics may include one or more filters that manage the broad band light to a plurality of desired wavelengths. The system controller 28 is configured (e.g., via stored instructions and in coordination with the light source 22 and the optics) to produce light beam centered on a predetermined wavelengths.

The produced light is directed to the tissue specimen. The incident light at each wavelength produces Raman scattered light. The Raman scattered light is received and dispersed/diffracted by the spectrometer 24 and detected by the light detector 26. The light detector 26 produces signals representative of the detected light and communicates those signals to the system controller 28. The system controller 28, in turn, processes the signals in the manner described herein, including using the classifier to identify/classify the tissue specimen.

While the principles of the disclosure have been described above in connection with specific apparatuses and methods, it is to be clearly understood that this description is made only by way of example and not as limitation on the scope of the disclosure. Specific details are given in the above description to provide a thorough understanding of the embodiments. However, it is understood that the embodiments may be practiced without these specific details.

It is noted that the embodiments may be described as a process which is depicted as a flowchart, a flow diagram, a block diagram, etc. Although any one of these structures may describe the operations as a sequential process, many of the operations can be performed in parallel or concurrently. In addition, the order of the operations may be rearranged. A process may correspond to a method, a function, a procedure, a subroutine, a subprogram, etc.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements unless the context clearly indicates otherwise. As used herein, "comprises" means "includes." Thus, "comprising A or B," means "including A or B, or A and B," without excluding additional elements.

It is noted that various connections are set forth between elements in the present description and drawings (the contents of which are included in this disclosure by way of reference). It is noted that these connections are general and, unless specified otherwise, may be direct or indirect and that this specification is not intended to be limiting in this respect. Any reference to attached, fixed, connected or the like may include permanent, removable, temporary, partial, full and/or any other possible attachment option.

No element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprise", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein. For example, in the exemplary embodiments described above within the Detailed Description portion of the present specification, elements may be described as individual units and shown as independent of one another to facilitate the description. In alternative embodiments, such elements may be configured as combined elements.

REFERENCES

1. A. S. Haka, et al., "In vivo margin assessment during partial mastectomy breast surgery using Raman spectroscopy", Cancer Res. 66(6), 3317-3322 (2006).
2. J. Mo, et al., "High wavenumber Raman spectroscopy for in vivo detection of cervical dysplasia", Anal. Chem. 81(21), 8908-8915 (2009).
3. K. Lin, et al., "Optical diagnosis of laryngeal cancer using high wavenumber Raman spectroscopy", Biosens. Bioelectron. 35(1), 213-217 (2012).
4. Aubertin et al., "Combining high wavenumber and fingerprint Raman spectroscopy for the detection of prostate cancer during radical prostatectomy", 9, (9), BIOMEDICAL OPTICS EXPRESS, p. 4294, (2018).
5. U.S. Pat. No. 7,499,153 issued to Puppels et al., "Use of High Wavenumber Raman Spectroscopy for Measuring Tissue".
6. U.S. Pat. No. 8,326,404 issued to Zeng et al., "Multimodal Detection of Tissue Abnormalities based on Raman and Background Fluorescence Spectroscopy".
7. Wang et al., "Simultaneous fingerprint and high-wavenumber fiber-optic Raman spectroscopy improves in vivo diagnosis of esophageal squamous cell carcinoma at endoscopy", Scientific Reports, 5, Article number: 12957 (2015).
8. R. Pandey et al, "Raman spectroscopy based molecular barcoding: realizing the value of high wavenumber region in breast cancer detection", Proc. SPIE 11631, Advanced Biomedical and Clinical Diagnostic and Surgical Guidance Systems XIX, 1163105 (5 Mar. 2021).

The invention claimed is:

1. A method of identifying tissue types that utilizes Raman scattered light in the high wavenumber region of Raman spectrum, comprising:
   interrogating a tissue specimen with at least one wavelength of light, the at least one wavelength of light operable to produce Raman scattered light in a high wavenumber (HWN) region of Raman spectrum from the tissue specimen upon the at least one wavelength of light being incident to the tissue;
   producing signal data representative of the Raman scattering, the signal data relating signal intensity as a function of wavenumber within the HWN region;
   wherein the signal data relating signal intensity as a function of wavenumber within the HWN region includes a plurality of signal intensity contributions, wherein each respective said signal intensity contribution is associated with a respective biomolecule present within the tissue;
   fitting a curve to a portion of the signal data attributable to the signal intensity contribution associated with a respective said biomolecule present within the tissue, for each of a plurality of the respective biomolecules present within the tissue, wherein each curve includes a fitted peak in the HWN region;
   determining a plurality of characteristics of each fitted curve; and
   determining a tissue type using the determined characteristics of the fitted curves and stored collective data representative of the fitted peaks in the HWN region of a plurality of different tissue types.

2. The method of claim 1, wherein the biomolecule present in the tissue specimen is a lipid, a protein, or a nucleic acid.

3. The method of claim 2, wherein the lipid present in the tissue specimen is a phospholipid or a fatty acid.

4. The method of claim 1, wherein the signal data relating signal intensity as said function of wavenumber is produced within a portion of the HWN region between about 2800 $cm^{-1}$ to about 3050 $cm^{-1}$.

5. The method of claim 1, wherein the plurality of characteristics of each fitted curve includes an area under the respective fitted curve.

6. The method of claim 1, wherein the step of determining said plurality of characteristics of each fitted curve includes determining an area plot for each of a plurality of different tissue types at one or more respective wavenumbers within the HWN region, wherein each area plot is based on the signal data relating signal intensity as a function of the respective wavenumber within the HWN region.

7. The method of claim 6, wherein the plurality of different tissue types includes adipose tissue, benign tissue, and cancer tissue.

8. The method of claim 7, wherein the plurality of different characteristics of each fitted curve as represented by said area plot includes at least one of an area, width, or height of the fitted curve.

9. The method of claim 1, wherein the stored collective data representative of fitted peaks in the HWN region of a plurality of different tissue types is based on data collected from a statistically significant number of tissue specimens.

10. The method of claim 1, wherein the step of determining said tissue type using the determined characteristics of the fitted curves may utilize machine learning or artificial intelligence.

11. A system for identifying tissue types, comprising:
   at least one light source;
   a spectrometer or a monochromator;
   at least one light detector; and
   a system controller in communication with the at least one light source, the at least one light detector, and a non-transitory memory storing instructions, which instructions when executed cause the system controller to:
control the at least one light source to interrogate a tissue specimen at one or more predetermined wavelengths;
control the at least one light detector to sense scattered light emanating from the tissue specimen after the scattered light has been processed by the spectrometer or the monochromator, the scattered light resulting from the light interrogation of the subject tissue, and to produce signal data representative of a Raman spectrum in the high wavenumber (HWN) region based on the sensed light;
wherein the signal data relates signal intensity as a function of wavenumber within the HWN region, the signal data including a plurality of signal intensity contributions, wherein each respective said signal intensity contribution is associated with a respective biomolecule present within the tissue;
process the signal data into processed signal data, wherein the processed signal data relates scattered light signal intensity as a function of wavenumber within the HWN region, the processed signal data including a plurality of signal intensity contributions, wherein each respective said signal intensity contribution is associated with a respective biomolecule present within the tissue;
fit a curve to a portion of the processed signal data attributable to the signal intensity contribution associated with a respective said biomolecule present within the tissue, for each of a plurality of the respective biomolecules present within the tissue, wherein each curve includes a fitted peak in the HWN region;
determine a plurality of characteristics of each fitted curve; and
determine a tissue type using the determined characteristics of the fitted curves and stored collective data representative of the fitted peaks in the HWN region of a plurality of different tissue types.

12. The system of claim 11, wherein the biomolecule present in the tissue specimen is a lipid, a protein, or a nucleic acid.

13. The system of claim 12, wherein the lipid present in the tissue specimen is a phospholipid or a fatty acid.

14. The system of claim 11, wherein the processed signal data relating signal intensity as said function of wavenumber is produced within a portion of the HWN region between about 2800 $cm^{-1}$ to about 3050 $cm^{-1}$.

15. The system of claim 11, wherein the plurality of characteristics of each fitted curve includes an area under the curve.

16. The system of claim 11, wherein the instructions when executed cause the system controller to determine an area plot for each of a plurality of different tissue types at one or more respective wavenumbers within the HWN region, wherein each area plot is based on the processed signal data relating signal intensity as a function of the respective wavenumber within the HWN region.

17. The system of claim 16, wherein the plurality of different tissue types includes adipose tissue, benign tissue, and cancer tissue.

18. The system of claim 17, wherein the plurality of different characteristics of each fitted curve as represented by said area plot includes at least one of an area, width, or height of the fitted curve.

19. The system of claim 11, wherein the stored collective data representative of fitted peaks in the HWN region of a plurality of different tissue types is based on data collected from a statistically significant number of tissue specimens.

20. The system of claim 11, wherein the determination of the tissue type utilizes machine learning or artificial intelligence.

21. A method of identifying tissue types that utilizes Raman scattered light in the high wavenumber region of Raman spectrum, comprising:
interrogating a tissue specimen with at least one wavelength of light, the at least one wavelength of light operable to produce Raman scattered light in a high wavenumber (HWN) region of Raman spectrum from the tissue specimen upon the at least one wavelength of light being incident to the tissue;
producing signal data representative of the Raman scattering, the signal data relating signal intensity as a function of wavenumber within the HWN region;
fitting a curve to a portion of the signal data attributable to a HWN peak within the signal data, for a plurality of different HWN peaks;
determining a plurality of characteristics of each fitted curve, including determining an area plot for each of a plurality of different tissue types at one or more respective wavenumbers within the HWN region, wherein each area plot is based on the signal data relating signal intensity as a function of the respective wavenumber within the HWN region; and
determining a tissue type using the determined characteristics of the fitted curves and stored collective data representative of fitted peaks in the HWN region of a plurality of different tissue types.

22. The method of claim 21, wherein the plurality of different characteristics of each fitted curve as represented by said area plot includes at least one of an area, width, or height of the fitted curve.

* * * * *